(12) United States Patent
Staskawics et al.

(10) Patent No.: US 6,579,677 B1
(45) Date of Patent: Jun. 17, 2003

(54) COMPOSITIONS AND METHODS FOR PLANT PATHOGEN RESISTANCE

(75) Inventors: Brian J. Staskawics, Castro Valley, CA (US); Karen S. Century, Berkeley, CA (US); Allan Shapiro, Newark, DE (US); Peter P. Repetti, Berkeley, CA (US); Douglas Dahlbeck, Castro Valley, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/427,774

(22) Filed: Oct. 26, 1999

Related U.S. Application Data (63) Continuation of application No. 08/975,628, filed on Nov. 21, 1997, now Pat. No. 6,166,295.
(60) Provisional application No. 60/033,206, filed on Nov. 22, 1996.

(51) Int. Cl.[7] .......................... C12Q 1/68; C12N 15/82; A01H 5/60; A61K 38/00; A61K 35/78
(52) U.S. Cl. .......................... 435/6; 800/279; 800/301; 514/2; 514/12; 514/13; 514/15; 530/324; 530/326; 530/328; 530/370; 530/379
(58) Field of Search ................................ 800/279, 301; 514/2, 12, 13, 15; 530/324, 326, 328, 370, 379; 435/6

(56) References Cited

FOREIGN PATENT DOCUMENTS

| WO | WO95 05731 | 3/1995 |
|----|------------|--------|
| WO | WO95 28423 | 10/1995 |

OTHER PUBLICATIONS

Century et al. NDR1, a locus of Arabidopsis thaliana that is required for disease resistance to both a bacterial and a fungal pathogen. 1995. (Proc. Natl. Acad. Sci. vol. 92. pp. 6597–6601), pp. 6597 (abstract), 6599–6601.*

Century et al. NDR1, a Pathogen–Induced Component Required for Arabidopsis Disease Resistance. 1997. (Science vol. 278: 1963–1965.*

Century et al., "NDR1, a locus of Arabidopsis thaliana that is required for disease resistance to both a bacterial and a fungal pathogen." Proceedings of the national Academy of Sciences of the United States of America, pp. 6597–6601 (1995).

Linthorst et al. The Plant Cell. 1989. Mar. Issue. vol. 1: 285–291.

Newman et al., 3321 Lambda–PRL2 Arabidopsis Thaliana cDNA Clone 95G3T7, see whole document (1994).

Newman, T., et al., Genes Galore: A Summary of Methods for Accessing Results from Large–Scale Partial Sequencing of Anonymous Araidopsis cDNA Clones, *Plant Physiol.* (1994( 106:1241–1255.

Sequence Listing Accession No. T21313 from the *Entrez* database (www.ncbi.nlm.nih.gov) linked to MEDLINE (Document No. 95148729), Newman et al., *Plant Physiol.* 106:1241–1255, 1994.

Shapiro et al., "Genetic Dissection of Signal Transduction in Arabidopsis Disease Resistance." Annual meeting of the 6th International Congress on Cell Biology and the 36th American Society of Cell Biology, San Francisco, California, U.S.A., Dec. 7–11, 1996. Molecular Biology of the Cell 7 (Suppl). 1996. 11A. ISSN: 1059–1524, XP002059803.

Tanksley et al. "Chromosome Landing: A Paradigm for Map–Based Gene Cloning in Plants with Large Genomes." Trends in Genetics, vol. 11, No. 2, pp. 63–68 (1995).

Thilmony et al., "Expression of the Tomato PTO Gene in Tobacco Enhances Resistance Topseudomonas Syringae PV TABACI Expressing AVRPTO," Plant Cell, vol. 7, pp. 1529–1536 (1995).

* cited by examiner

Primary Examiner—Christopher S. F. Low
Assistant Examiner—Billy D. Chism
(74) Attorney, Agent, or Firm—Klarquist Sparkman, LLP (57) ABSTRACT

The NDR1 gene of *Arabidopsis thaliana* has been cloned and sequenced. NDR1 is necessary for plant defense mediated by numerous disease resistance gene products. Expression of NDR1 in transgenic plants confers resistance to a broad variety of plant pathogens.

15 Claims, 4 Drawing Sheets

Days after innoculation

```
TTTGTTATGT ATTTGGCTAA ACGCGTGTGT GCGTGTGTGT CCTACTGAGT CGTCTCTTTT

GAGTCAACTT GAAATATCAA CCAATCAGCA AACCAAAATC TTATAACATC ATCTTCTTCA

TCTTTCCGAC AAAAATACCA AATTCTTGAA AACAAAAAAA AAATGAATAA TCAAAATGAA
                                                     M  N  N     Q  N  E
GACACAGAAG GTGGTCGAAA CTGTTGTACT TGCTGCTTAA GCTTCATCTT CACAGCTGGT
 D  T  E   G  G  R  N   C  C  T   C  C  L    S  F  I  F   T  A  G
            10                                          20
CTCACCTCTC TTTTCTTATG GCTTAGTCTC CGTGCGGACA AACCCAAATG CTCAATCCAA
 L  T  S   L  F  L  W   L  S  L   R  A  D    K  P  K  C    S  I  Q
         30                                         40
AACTTTTTCA TTCCTGCCCT CGGAAAAGAC CCAAATTCAC GAGACAATAC CACTCTAAAT
 N  F  F   I  P  A  L   G  K  D    P  N  S   R  D  N  T    T  L  N
         50                                         60
TTCATGGTTC GTTGTGACAA TCCGAATAAA GACAAAGGAA TCTACTACGA CGATGTCCAC
 F  M  V   R  C  D  N    P  N  K   D  K  G    I  Y  Y  D   D  V  H
         70                                         80
CTTAATTTTT CCACCATCAA CACGACCAAG ATCAATTCAT CTGCTCTTGT CTTAGTTGGT
 L  N  F   S  T  I  N   T  T  K    I  N  S    S  A  L  V   L  V  G
         90                                         100
AACTACACAG TGCCTAAGTT CTATCAAGGA CACAAGAAGA AGGCCAAGAA GTGGGGTCAA
 N  Y  T   V  P  K  F    Y  Q  G    H  K  K   K  A  K  K   W  G  Q
         110                                        120
GTAAAGCCGC TAAACAACCA GACGGTTTTA CGAGCGGTTT TGCCTAATGG ATCGGCTGTT
 V  K  P   L  N  N  Q    T  V  L   R  A  V    L  P  N  G   S  A  V
         130                                        140
TTCAGGTTGG ATCTCAAGAC TCAAGTTAGA TTCAAGATTG TTTTTTGGAA AACTAAGAGG
 F  R  L   D  L  K  T    Q  V  R    F  K  I   V  F  W  K    T  K  R
         150                                        160
TATGGGGTTG AAGTTGGAGC TGATGTTGAA GTCAACGGTG ATGGAGTTAA AGCTCAGAAG
 Y  G  V   E  V  G  A    D  V  E    V  N  G   D  G  V  K    A  Q  K
         170                                        180
AAAGGAATTA AGATGAAGAA ATCTGATTCT TCTTTTCCAT TAAGAAGCTC TTTTCCGATT
 K  G  I   K  M  K  K    S  D  S    S  F  P   L  R  S  S    F  P  I
         190                                        200
AGTGTTTTGA TGAATTTACT CGTATTCTTT GCTATTCGTT AACTTCATTA ATGGTGTTGA
 S  V  L   M  N  L  L    V  F  F   A  I  R
         210
TTTTCAGGTT TTTCATTTCT TGGTTTTGTT GATTTTGATT ATTGACTATT TCATGAGTTT

TGTTGTGATC CTTAGTTCCA TTTTCTTCAT TGCATAATTT ATCCCTTATT TTTTTTGTTT
```

FIG. 4

SEQUENCE LISTING

<160> NUMBER OF SEQ ID NOS: 2

<210> SEQ ID NO 1
<211> LENGTH: 960
<212> TYPE: DNA
<213> ORGANISM: Arabidopsis thaliana
<220> FEATURE:
<221> NAME/KEY: CDS
<222> LOCATION: (163)..(822)

<400> SEQUENCE: 1

```
tttgttatgt atttggctaa acgcgtgtgt gcgtgtgtgt cctactgagt cgtctctttt    60
gagtcaactt gaaatatcaa ccaatcagca aaccaaaatc ttataacatc atcttcttca   120
tctttccgac aaaaatacca aattcttgaa acaaaaaaaa aa atg aat aat caa      174
                                                 Met Asn Asn Gln
                                                  1 aat gaa gac aca gaa ggt ggt cga aac tgt tgt act tgc tgc tta agc    222
Asn Glu Asp Thr Glu Gly Gly Arg Asn Cys Cys Thr Cys Cys Leu Ser
  5              10                  15                  20 ttc atc ttc aca gct ggt ctc acc tct ctt ttc tta tgg ctt agt ctc    270
Phe Ile Phe Thr Ala Gly Leu Thr Ser Leu Phe Leu Trp Leu Ser Leu
              25                  30                  35 cgt gcg gac aaa ccc aaa tgc tca atc caa aac ttt ttc att cct gcc    318
Arg Ala Asp Lys Pro Lys Cys Ser Ile Gln Asn Phe Phe Ile Pro Ala
          40                  45                  50 ctc gga aaa gac cca aat tca cga gac aat acc act cta aat ttc atg    366
Leu Gly Lys Asp Pro Asn Ser Arg Asp Asn Thr Thr Leu Asn Phe Met
      55                  60                  65 gtt cgt tgt gac aat ccg aat aaa gac aaa gga atc tac tac gac gat    414
Val Arg Cys Asp Asn Pro Asn Lys Asp Lys Gly Ile Tyr Tyr Asp Asp
  70                  75                  80 gtc cac ctt aat ttt tcc acc atc aac acg acc aag atc aat tca tct    462
Val His Leu Asn Phe Ser Thr Ile Asn Thr Thr Lys Ile Asn Ser Ser
 85                  90                  95                 100 gct ctt gtc tta gtt ggt aac tac aca gtg cct aag ttc tat caa gga    510
Ala Leu Val Leu Val Gly Asn Tyr Thr Val Pro Lys Phe Tyr Gln Gly
                 105                 110                 115 cac aag aag aag gcc aag aag tgg ggt caa gta aag ccg cta aac aac    558
His Lys Lys Lys Ala Lys Lys Trp Gly Gln Val Lys Pro Leu Asn Asn
             120                 125                 130 cag acg gtt tta cga gcg gtt ttg cct aat gga tcg gct gtt ttc agg    606
Gln Thr Val Leu Arg Ala Val Leu Pro Asn Gly Ser Ala Val Phe Arg
         135                 140                 145 ttg gat ctc aag act caa gtt aga ttc aag att gtt ttt tgg aaa act    654
Leu Asp Leu Lys Thr Gln Val Arg Phe Lys Ile Val Phe Trp Lys Thr
     150                 155                 160 aag agg tat ggg gtt gaa gtt gga gct gat gtt gaa gtc aac ggt gat    702
Lys Arg Tyr Gly Val Glu Val Gly Ala Asp Val Glu Val Asn Gly Asp
 165                 170                 175                 180 gga gtt aaa gct cag aag aaa gga att aag atg aag aaa tct gat tct    750
Gly Val Lys Ala Gln Lys Lys Gly Ile Lys Met Lys Lys Ser Asp Ser
                 185                 190                 195 tct ttt cca tta aga agc tct ttt ccg att agt gtt ttg atg aat tta    798
Ser Phe Pro Leu Arg Ser Ser Phe Pro Ile Ser Val Leu Met Asn Leu
             200                 205                 210 ctc gta ttc ttt gct att cgt taa cttcattaat ggtgttgatt ttcaggtttt   852
Leu Val Phe Phe Ala Ile Arg
         215                 220
```

-continued

```
tcatttcttg gttttgttga ttttgattat tgactatttc atgagttttg ttgtgatcct    912
tagttccatt ttcttcattg cataatttat cccttatttt ttttgttt               960
```

<210> SEQ ID NO 2
<211> LENGTH: 219
<212> TYPE: PRT
<213> ORGANISM: Arabidopsis thaliana

<400> SEQUENCE: 2

```
Met Asn Asn Gln Asn Glu Asp Thr Glu Gly Gly Arg Asn Cys Cys Thr
 1               5                  10                  15

Cys Cys Leu Ser Phe Ile Phe Thr Ala Gly Leu Thr Ser Leu Phe Leu
            20                  25                  30

Trp Leu Ser Leu Arg Ala Asp Lys Pro Lys Cys Ser Ile Gln Asn Phe
        35                  40                  45

Phe Ile Pro Ala Leu Gly Lys Asp Pro Asn Ser Arg Asp Asn Thr Thr
    50                  55                  60

Leu Asn Phe Met Val Arg Cys Asp Asn Pro Asn Lys Asp Lys Gly Ile
65                  70                  75                  80

Tyr Tyr Asp Asp Val His Leu Asn Phe Ser Thr Ile Asn Thr Thr Lys
                85                  90                  95

Ile Asn Ser Ser Ala Leu Val Leu Val Gly Asn Tyr Thr Val Pro Lys
            100                 105                 110

Phe Tyr Gln Gly His Lys Lys Lys Ala Lys Lys Trp Gly Gln Val Lys
        115                 120                 125

Pro Leu Asn Asn Gln Thr Val Leu Arg Ala Val Leu Pro Asn Gly Ser
    130                 135                 140

Ala Val Phe Arg Leu Asp Leu Lys Thr Gln Val Arg Phe Lys Ile Val
145                 150                 155                 160

Phe Trp Lys Thr Lys Arg Tyr Gly Val Glu Val Gly Ala Asp Val Glu
                165                 170                 175

Val Asn Gly Asp Gly Val Lys Ala Gln Lys Lys Gly Ile Lys Met Lys
            180                 185                 190

Lys Ser Asp Ser Ser Phe Pro Leu Arg Ser Ser Phe Pro Ile Ser Val
        195                 200                 205

Leu Met Asn Leu Leu Val Phe Phe Ala Ile Arg
    210                 215
```

COMPOSITIONS AND METHODS FOR PLANT PATHOGEN RESISTANCE

CROSS REFERENCE TO RELATED CASE

This is a continuation of application Ser. No. 08/975,628, filed Nov. 21, 1997, now U.S. Pat. No. 6,166,295, and claims the benefit of U.S. Provisional Application No. 60/033,206, filed Nov. 22, 1996.

ACKNOWLEDGMENT OF GOVERNMENT SUPPORT

This invention was made with Government support under grant (contract) no. MCB-9219959 awarded by the National Science Foundation. The Government has certain rights to this invention.

BACKGROUND OF THE INVENTION

This invention relates to plant disease resistance, in particular to plant genes conferring pathogen resistance.

Whether a plant is resistant or susceptible to attack by a given pathogen is frequently under the control of a single, dominant resistance gene (Flor, *Annu. Rev. Phytopathol.* 9:275–296, 1971). Resistance gene products are thought to recognize signal molecules produced by the pathogen and respond by initiating rapid changes in host cell physiology and metabolism that directly inhibit pathogen growth.

Classic genetic analyses of disease resistance in plants have demonstrated that resistance to pathogens is often highly specific, requiring single corresponding genetic loci in both the plant and the pathogen. Several plant genes corresponding to these resistance loci have recently been cloned and characterized. The Pto gene from tomato, which confers resistance to *Pseudomonas syringae* pv. *tomato*, encodes a serine-threonine protein kinase (Martin et al., *Science* 262:1432–1436, 1993). The RPS2, RPM1 and RPP5 genes from Arabidopsis (Bent et al., *Science* 265:1856–1860, 1994; Mindrinos et al., *Cell* 78:1089–1099, 1994; Grant et al., *Science* 269:843–846, 1995), the N gene from tobacco (Whitham et al., *Cell* 78:1101–1115, 1994), and the L6 gene from flax (Lawrence et al., *Plant Cell* 7:1195–1206, 1995) all have several motifs suggestive of signaling roles for these proteins. These motifs include nucleotide binding sites (NBSs) and leucine-rich repeats (LRRs); thus, these proteins are commonly referred to as the NBS/LRR class. LRR motifs have been implicated in protein-protein interactions (Kobe and Deisenhofer, *Trends Biochem. Sci.* 19:415–421, 1994), raising the possibility that the LRR portion of these resistance gene products is required for specific recognition of a protein elicitor, or for interaction with other protein components of a signal transduction pathway. RPP5, L6 and N also contain N-terminal domains with homology to the mammalian interleukin 1 receptor (IL-1R) and the Drosophila Toll gene. These genes encode transmembrane receptor tyrosine kinases that act upstream of the rel family transcription factors NF-κB and Dorsal. A kinase with high levels of homology to Pto—the Pelle gene product—functions downstream of Toll in Drosophila.

It is possible that molecular recognition of an avirulent pathogen requires proteins with all of these motifs. The identification of Prf, an NBS/LRR protein required for function of the Pto gene, and of Xa-21, a gene that confers resistance to bacterial blight of rice and has both an LRR and a kinase domain, supports this hypothesis. This striking similarity between genes that confer resistance to bacterial, viral and fungal pathogens suggests that mechanisms of resistance are conserved within and among different plant species. Therefore, the signal transduction pathways utilized by the different resistance gene products may converge at some common step. However, genes that integrate different upstream molecular recognition signals and activate a hypothetical common downstream resistance pathway have not been previously identified.

SUMMARY OF THE INVENTION

We have identified a gene in *Arabidopsis thaliana* that encodes a pathogen-induced signal integrator required for disease resistance, referred to herein as NDR1. The nucleotide sequence of a genomic clone of NDR1 and the corresponding amino acid sequence are provided. The NDR1 gene is required for resistance to the bacterial pathogen *Pseudomonas syringae* pv. *tomato* (*Pst*) and the fungal pathogen *Peronospora parasitica*, among others. Expression of NDR1 in transgenic plants confers resistance to a broad variety of plant pathogens, including, but not limited to, bacteria, viruses, fungi, nematodes, and other plant pathogens. According to one aspect of the present invention, isolated nucleic acids are provided that include a promoter that is expressible in a plant cell, and, operably linked to the promoter, (a) a polynucleotide comprising at least 100 consecutive nucleotides having at least 70% nucleotide sequence similarity with SEQ ID NO:1; or (b) a polynucleotide that encodes a polypeptide of at least 100 amino acid residues having at least 70% amino acid sequence similarity with SEQ ID NO:2. Preferably, the polynucleotide includes only silent nucleotide sequence changes to the NDR1 sequence of SEQ ID NO:1 or changes that result in conservative amino acid substitutions. Since NDR1 has two putative transmembrane domains, preferably the polynucleotide encodes two transmembrane domains. Transformation of a plant cell with the polynucleotide sequence increases resistance of the plant cell to the pathogen.

Therefore, according to another aspect of the invention, transgenic plants are provided that comprise nucleic acids as described above. Such transgenic plants can be produced by introducing such nucleic acids into the cell of a plant, thereby producing a transformed plant cell, and regenerating the transformed cell to produce a transgenic plant. As discussed in the Example, such transgenic plants display greater pathogen resistance than control plants.

Alleles and homologs of the NDR1 gene from Arabidopsis accession Col-0 can be obtained, for example, by contacting a plurality of polynucleotides of a plant other than Arabidopsis accession Col-0 with a probe or primer comprising at least 15 contiguous nucleotides of SEQ ID NO:1 under at least moderately stringent hybridization conditions, to permit the probe or primer to hybridize to an NDR1 polynucleotide of the plant, and isolating the NDR1 polynucleotide of the plant species to which the probe or primer hybridizes. For example, a plant cDNA or genomic library can be screened with a NDR1 probe that includes a detectable label. Alternately, an amplification reaction (e.g., the polymerase chain reaction, PCR) can be performed on the plant's mRNA, cDNA, or genomic DNA to produce an amplified NDR1 polynucleotide, which can be isolated.

The availability of the cloned NDR1 gene also makes it possible to produce isolated NDR1 polypeptides, e.g., by recombinant expression of NDR1 constructs in host cells. NDR1-specific antibodies can be raised against purified NDR1 and used, for example, for purifying NDR1 polypeptides, in immunoassays, and for expression cloning efforts.

The foregoing and other aspects of the invention will become more apparent from the following detailed description and accompanying drawings.

SEQUENCE LISTING

The nucleic acid and amino acid sequences listed in the accompanying Sequence Listing are shown using standard letter abbreviations for nucleotide bases and three letter codes for amino acids. Only one strand of each nucleic acid sequence is shown, but the complementary strand is understood to be included by any reference to the displayed strand.

SEQ ID NO: 1 shows a nucleotide sequence encoding an NDR1 polypeptide.

SEQ ID NO: 2 shows the amino acid sequence of an NDR1 polypeptide.

BRIEF DESCRIPTION OF THE DRAWINGS

FIGS. 1A–C show corresponding genetic and physical maps of the genomic region of *Arabidopsis thaliana* containing the NDR1 gene related to the positional cloning of NDR1.

FIGS. 2A–B show growth of avirulent *Pst* strain DC3000 within cosmid-complemented ndr1-1 Arabidopsis. FIG. 2A: *Pst* DC3000 (avrRpt2). FIG. 2B: *Pst* DC3000 (avrRpm1). -●- ndr1-1 mutant, -■- ndr1-1 transformed with non-complementing CB17 cosmid, -○-wild-type Col-0, -□- ndr1-1 transformed with complementing FH6 cosmid. Sample means and standard deviations are shown from a representative experiment.

FIG. 3 shows the nucleotide sequence of the NDR1 gene (SEQ ID NO: 1) and the deduced amino-acid sequence of the NDR1 protein (SEQ ID NO: 2).

FIG. 4 shows the primary structure of the NDR1 predicted protein (SEQ ID NO: 2). Putative transmembrane domains are underlined. The N-terminal portion of the protein through amino acid N-179 that is deleted in ndr1-1 is indicated by an arrow. Molecular alterations in ethylmethane sulfonate (EMS)-induced mutant ndr1-2 and gamma ray-induced mutant ndr1-3 alleles that convert W-124 and F-31, respectively, and premature stop codons are indicated by asterisks.

DETAILED DESCRIPTION OF THE INVENTION

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: N.Y., 1991; and Lewin, *Genes V*, Oxford University Press: New York, 1994.

The Genetic Basis for Resistance to Pathogens

Following the invasion of a plant by a potential pathogen, the pathogen either successfully proliferates in the host, causing associated disease symptoms, or its growth is halted by the defenses of the host plant. One such defense is the hypersensitive response (HR), a rapid cellular necrosis near the site of the infection that correlates with the generation of activated oxygen species, production of antimicrobial compounds, and reinforcement of host cell walls (Dixon and Lamb, *Annu. Rev. Plant Physiol. Plant Mol. Biol.* 41:339–367, 1990). Other defenses include systemic acquired resistance, which effectively protects the plant against subsequent attack by a broad range of pathogens (Ryals et al., *Proc. Natl. Acad. Sci. USA* 92:4202–4205, 1995).

Pathogens that elicit an HR on a given host are "avirulent" on that host, the host is "resistant," and the plant-pathogen interaction is "incompatible." If a pathogen proliferates and causes disease on the host, the pathogen is "virulent," the host is "susceptible," and the plant-pathogen interaction is "compatible."

In many cases in which strains ("races") of a particular fungal or bacterial pathogen differ regarding virulence on various cultivars (or wild accessions) of a particular host species, avirulent strains of the pathogen, but not virulent strains, possess one or more avirulence (avr) genes corresponding to "resistance" genes in the host. This observation is the basis for the "gene-for-gene" model of plant disease resistance (Crute et al., pp. 197–309 in *Mechanisms of Resistance to Plant Disease*, Fraser, ed., 1985; Ellingboe, *Annu. Rev. Phytopathol.* 19:125–143, 1981; Flor, *Annu. Rev. Phytopathol.* 9:275–296, 1971; and Keen et al., in *Application of Biotechnology to Plant Pathogen Control*, Chet, ed., John Wiley & Sons, 1993, pp. 65–88).

Normally avirulence and resistance genes are organized in functional pairs. A given resistance gene is generally effective only against pathogen strains that express a specific cognate avirulence gene (Flor, *Annu. Rev. Phytopathol.* 9:275–296, 1971; Keen, *Annu. Rev. Genet.* 24:447–463, 1990). However, exceptions to this rule exist. For example the Arabidopsis RPM1 gene product (Grant et al., *Science* 269:843–846, 1995) is involved in the recognition of elicitors produced by *P. syringae* expressing the avirulence genes avrRpm1 or avrB (Bisgrove et al., *Plant Cell* 6:927–933, 1994), suggesting that resistance gene products may function as common points in transduction of distinct pathogen signals.

Resistance gene products are activated in response to pathogen signal molecules termed elicitors, production of which is controlled by pathogen avirulence genes.

A number of avirulence genes have been cloned (Long and Staskawicz, *Cell* 73:921–935, 1993; Dangl, in *Bacterial Pathogenesis of Plants and Animals*, Dangl, ed., Springer-Verlag, 1994, pp. 99–118; Innes et al., *J. Bacteriol.* 175:4859–4869, 1993; Dong et al., *Plant Cell* 3:61–72, 1991; Whelan et al., *Plant Cell* 3:49–59, 1991; Staskawicz et al., *J. Bacteriol.* 169:5789–5794, 1987; Gabriel et al., *Proc. Natl. Acad. Sci. USA* 83:6415–6419, 1986; Keen and Staskawicz, *Annu. Rev. Microbiol.* 42:421–440, 1988; Kobayashi et al., *Mol. Plant-Microbe Interact.* 3:94–102 and 3:103–111, 1990). Many cloned avirulence genes have been shown to correspond to individual resistance genes in the cognate host plants and confer an avirulent phenotype when transferred to an otherwise virulent strain.

Examples of known signals to which plants respond when infected by pathogens include hairpins from Erwinia (Wei et al., *Science* 257:85–88, 1992) and Pseudomonas (He et al., *Cell* 73:1255–1266, 1993); avr4 (Joosten et al., *Nature* 367:384–386, 1994) and avr9 peptides (van den Ackerveken et al., *Plant J.* 2:359–366, 1992) from Cladosporium; PopA1 from Pseudomonas (Arlat et al., *EMBO J.* 13:543–553, 1994); avrD-generated lipopolysaccharide (Midland et al., *J. Org. Chem.* 58:2940–2945, 1993); and NIP1 from Rhynchosporium (Hahn et al., *Mol. Plant-Microbe Interact.* 6:745–754, 1993).

A number of plant disease resistance genes have also been cloned (Bent et al., *Science* 265:1856–1860, 1994; Grant et al., *Science* 269:843–846, 1995; Jones et al., *Science* 266:789–792, 1994; Martin et al., *Science* 262:1432–1436, 1993; Mindrinos et al., *Cell* 78:1089–1099, 1994; Song et al., *Science* 270:1804–1806, 1995; Whitham et al., *Cell* 78:1101–1115, 1994).

Similar features have been discovered among many of these resistance genes in spite of the diversity of pathogens against which they act. These features include a leucine-rich-repeat (LRR), a motif found in a multitude of eukaryotic proteins with roles in signal transduction (Kobe and Deisenhofer, *Trends Biochem. Sci.* 19:415–421, 1994). The LRR motif is thought to be involved in protein-protein interactions and may allow interaction with other proteins that are involved in plant disease resistance. In addition, sequences predicted to encode nucleotide binding sites and leucine zippers are shared among many resistance genes (Dangl, *Cell* 80:383–386, 1995; Staskawicz et al., *Science* 268:661–667, 1995). These motifs are present and similarly organized among resistance gene products from plants as diverse as tobacco, tomato, rice, flax, and Arabidopsis, suggesting a common mechanism underlying disease resistance signal transduction throughout the plant kingdom.

A race-specific resistance gene from *Zea mays* (corn), Hm1 (Johal and Briggs, *Science* 258:985–987, 1992), confers resistance against specific races of the fungal pathogen *Cochliobolus carbonum* by controlling degradation of a fungal toxin. This strategy is mechanistically distinct from the avirulence-gene specific resistance mechanism described above.

Nucleic Acids

"Polynucleotide". A polynucleotide or nucleic acid sequence is a naturally-occurring or chemically-synthesized DNA or RNA sequence. A polynucleotide according to the invention may be single- or double-stranded.

"NDR1 Polynucleotide"; "NDR1 Gene". The terms "NDR1 polynucleotide" or "NDR1 gene" refer to a native NDR1-encoding polynucleotide or a fragment thereof, e.g., a native *Arabidopsis thaliana* cDNA (SEQ ID NO:1) or genomic sequence or alleles thereof, or NDR1 homologs from other plant species. The terms also encompass variant or modified forms of a native NDR1 nucleic acid sequence or fragment thereof as discussed below, preferably a polynucleotide that encodes a polypeptide having NDR1 biological activity.

Native NDR1 sequences include 5'- and 3'-flanking sequences or internal sequences operably linked to a native NDR1 polynucleotide sequence, including regulatory elements and/or intron sequences.

"NDR1 Biological Activity". The term "NDR1 biological activity" refers to a biological activity characteristic of a native NDR1 polypeptide. In *Arabidopsis thaliana*, the NDR1 gene product required for resistance to certain plant pathogens such as *Pseudomonas syringae* pv. *tomato* and *Peronospora parasitica*. The cloned NDR1 polynucleotide disclosed herein (FIG. 3; SEQ ID NO:1) also has the biological activity of complementing the ndr1-1 mutant of *Arabidopsis thaliana*, thereby restoring resistance to *Pseudomonas syringae* pv. *tomato, Pseudomonas syringae* pv. *maculicola, Peronospora parasitica*, and other pathogens.

"Disease Resistance Gene". The term "disease resistance gene" refers to a plant gene such as NDR1 that encodes a polypeptide capable of triggering the defense response of a plant cell or tissue to infection by a pathogen to which the plant would otherwise be susceptible.

"Native". The term "native" refers to a naturally-occurring ("wild-type") nucleic acid or polypeptide.

"Allele". An allele is one of two or more alternative forms of a gene that occupy the same locus in a particular chromosome or linkage structure and that differ from other alleles of the locus at one or more base pairs as a result of mutation.

"Homolog". A "homolog" of NDR1 is a polynucleotide from a plant species other than *Arabidopsis thaliana* that encodes a polypeptide that is functionally similar to NDR1 and that preferably has substantial amino acid sequence similarity to NDR1 of Arabidopsis (SEQ ID NO:1).

"Isolated". An "isolated" nucleic acid is one that has been substantially separated or purified away from other nucleic acid sequences in the cell of the organism in which the nucleic acid naturally occurs, i.e., other chromosomal and extrachromosomal DNA and RNA, by conventional nucleic acid-purification methods. The term also embraces recombinant nucleic acids and chemically synthesized nucleic acids.

Fragments, Probes, and Primers. A fragment of an NDR1 polynucleotide is a portion of an NDR1 polynucleotide that is less than full-length and comprises at least a minimum length capable of hybridizing specifically with a native NDR1 polynucleotide under stringent hybridization conditions. The length of such a fragment is preferably at least 15 nucleotides, more preferably at least 20 nucleotides, and most preferably at least 30 nucleotides of a native NDR1 polynucleotide.

Nucleic acid probes and primers can be prepared based on a native NDR1 polynucleotide. A "probe" is an isolated polynucleotide to which is attached a conventional detectable label or reporter molecule, e.g., a radioactive isotope, ligand, chemiluminescent agent, or enzyme. A "primer" is an isolated polynucleotide that can be annealed to a complementary target DNA strand by nucleic acid hybridization to form a hybrid between the primer and the target polynucleotide strand, then extended along the target polynucleotide strand by a polymerase, e.g., a DNA polymerase. Primer pairs can be used for amplification of a polynucleotide sequence, e.g., by the polymerase chain reaction (PCR) or other conventional amplification methods.

Probes and primers are generally 15 nucleotides or more in length, preferably 20 nucleotides or more, more preferably 25 nucleotides, and most preferably 30 nucleotides or more. Such probes and primers hybridize specifically to a native *Arabidopsis thaliana* NDR1 polynucleotide under high stringency hybridization conditions and hybridize specifically to a native NDR1 sequence of another species under at least moderately stringent conditions. Preferably, probes and primers according to the present invention have complete sequence identity with the native NDR1 sequence.

Methods for preparing and using probes and primers are described; for example, in *Molecular Cloning: A Laboratory Manual*, 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the native NDR1 sequence disclosed herein can be used to confirm (and, if necessary, to correct) the disclosed NDR1 nucleotide sequence (FIG. 3; SEQ ID NO:1) by conventional methods, e.g., by re-cloning and sequencing an NDR1 cDNA or genomic sequence.

Substantial Similarity. A first nucleic acid is "substantially similar" to a second nucleic acid if, when optimally aligned (with appropriate nucleotide insertions or deletions) with the other nucleic acid (or its complementary strand), there is at least about 75% nucleotide sequence similarity, preferably at least about 80%, more preferably at least about 90%, and most preferably at least about 95% identity. Preferably, such substantial similarity exists over at least 100 base pairs, more preferably over the entire protein coding region. Sequence similarity can be determined by comparing the nucleotide sequences of two nucleic acids using sequence analysis software such as the Sequence Analysis Software Package of the Genetics Computer Group, University of Wisconsin Biotechnology Center, Madison, Wis.

Alternatively, two nucleic acids are substantially similar if they hybridize under stringent conditions, as defined below.

"Operably Linked". A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked DNA sequences are contiguous and, where necessary to join two protein coding regions, in reading frame.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic-acid manipulation are well-known (see, e.g., Sambrook et al., 1989, and Ausubel et al., 1992). Methods for chemical synthesis of nucleic acids are discussed, for example, in Beaucage and Carruthers, *Tetra. Letts.* 22:1859–1862, 1981, and Matteucci et al., *J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic acids; Vectors, Transformation, Host cells. Natural or synthetic nucleic acids according to the present invention can be incorporated into recombinant nucleic-acid constructs, typically DNA constructs, capable of being introduced into, and replicating in, a host cell. Such a construct preferably is a vector that includes a replication system and sequences that are capable of transcription and translation of a polypeptide-encoding sequence in a given host cell.

For the practice of the present invention, conventional compositions and methods for preparing and using vectors and host cells are employed, as discussed, inter alia, in Sambrook et al., 1989, or Ausubel et al., 1992.

A cell, tissue, organ, or organism into which has been introduced a foreign nucleic acid, such as a recombinant vector, is considered "transformed", "transfected", or "transgenic." A "transgenic" or "transformed" cell or organism also includes progeny of the cell or organism and progeny produced from a breeding program employing such a "transgenic" plant as a parent in a cross and exhibiting an altered phenotype resulting from thepresence of a recombinant NDR1 nucleic acid construct.

A number of vectors suitable for stable transfection of plant cells or for the establishment of transgenic plants have been described in, e.g., Pouwels et al., *Cloning Vectors: A Laboratory Manual*, 1985, supp. 1987); Weissbach and Weissbach, *Methods for Plant Molecular Biology*, Academic Press, 1989; and Gelvin et al., *Plant Molecular Biology Manual*, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Examples of constitutive plant promoters useful for expressing NDR1 polynucleotides include but are not limited to: the cauliflower mosaic virus (CaMV) 35S promoter, which confers constitutive, high-level expression in most plant tissues (see, e.g., Odel et al., *Nature* 313:810, 1985), including monocots (see, e.g., Dekeyser et al., *Plant Cell* 2:591, 1990; Terada and Shimamoto, *Mol. Gen. Genet.* 220:389, 1990); the nopaline synthase promoter (An et al., *Plant Physiol.* 88:547, 1988) and the octopine synthase promoter (Fromm et al., *Plant Cell* 1:977, 1989).

A variety of plant gene promoters that are regulated in response to environmental, hormonal, chemical, and/or developmental signals, also can be used for expression of an NDR1 polynucleotide in plant cells, including promoters regulated by: (1) heat (Callis et al., *Plant Physiol.* 88:965, 1988); (2) light (e.g., pea rbcS-3A promoter, Kuhlemeier et al., *Plant Cell* 1:471, 1989; maize rbcS promoter, Schaffner and Sheen, *Plant Cell* 3:997, 1991; or chlorophyll a/b-binding protein promoter, Simpson et al., *EMBO J*. 4:2723, 1985); (3) hormones, such as abscisic acid (Marcotte et al., *Plant Cell* 1:969, 1989); (4) wounding (e.g., wunI, Siebertz et al., *Plant Cell* 1:961, 1989); or (5) chemicals such as methyl jasminate, salicylic acid, or Safener. It may also be advantageous to employ organ-specific promoters (e.g., Roshal et al., *EMBO J*. 6:1155, 1987; Schernthaner et al., *EMBO J*. 7:1249, 1988; Bustos et al., *Plant Cell* 1:839, 1989).

Plant expression vectors optionally include RNA processing signals, e.g., introns, which may be positioned upstream or downstream of a protein-coding sequence in the transgene. In addition, the expression vectors may also include additional regulatory sequences from the 3'-untranslated region of plant genes (Thornburg et al., *Proc. Natl. Acad. Sci. USA* 84:744 (1987); An et al., *Plant Cell* 1:115 (1989), e.g., a 3' terminator region to increase mRNA stability of the mRNA, such as the PI–II terminator region of potato or the octopine or nopaline synthase 3' terminator regions.

Useful dominant selectable marker genes include genes encoding antibiotic resistance genes (e.g., resistance to hygromycin, kanamycin, bleomycin, G418, streptomycin or spectinomycin); and herbicide resistance genes (e.g., phosphinothricin acetyltransferase). A useful strategy for selection of transformants for herbicide resistance is described, e.g., in Vasil, *Cell Culture and Somatic Cell Genetics of Plants*, Vols. I–III, Laboratory Procedures and Their Applications Academic Press, New York, 1984.

Nucleic-Acid Hybridization; "Stringent Conditions"; "Specific". The nucleic-acid probes and primers of the present invention hybridize under stringent conditions to a target DNA sequence, e.g., to a native NDR1 polynucleotide.

The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989 at 9.47–9.52, 9.56–9.58; Kanehisa, *Nucl. Acids Res.* 12:203–213, 1984; and Wetmur and Davidson, *J. Mol. Biol.* 31:349–370, 1968.

Regarding the amplification of a target nucleic-acid sequence (e.g., by PCR) using a particular amplification primer pair, "stringent conditions" are conditions that permit the primer pair to hybridize substantially only to the target nucleic-acid sequence to which a primer having the corresponding wild-type sequence (or its complement) would bind so as to produce a unique amplification product.

For hybridization of a probe or primer to a polynucleotide of another plant species in order to identify NDR1 homologs, preferred hybridization and washing conditions are as discussed in Sambrook et al., 1989 at 9.47–9.57, wherein "high stringency hybridization conditions" include hybridization at 65° C. in a hybridization solution that includes 6×SSC and washing for 1 hour at 65° C. in a wash solution that includes 0.5×SSC, 0.5% SDS. "Moderate stringency" conditions are similar except that the temperature for the hybridization and washing steps are performed at a lower temperature at which the probe is specific for a target sequence, preferably at least 42° C., more preferably at least 50° C., more preferably at 55° C., and most preferably at least 60° C.

The term "specific for (a target sequence)" indicates that a probe or primer hybridizes under given hybridization conditions substantially only to the target sequence in a sample comprising the target sequence.

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990.

Nucleotide- and Amino-Acid Seauence Variants. Using the NDR1 nucleotide and amino-acid sequences disclosed herein (FIG. 3; SEQ ID NO:1), those skilled in the art can create polynucleotides and polypeptides that have minor sequence variations from the corresponding native sequence.

"Variant" polynucleotides are polynucleotides containing minor changes in a native NDR1 polynucleotide sequence, i.e., changes in which one or more nucleotides of a native NDR1 polynucleotide is deleted, added, and/or substituted, preferably while substantially maintaining a biological activity of NDR. Variant polynucleotides can be produced, for example, by standard DNA mutagenesis techniques or by chemically synthesizing the variant polynucleotide molecule or a portion thereof. Such variants preferably do not change the reading frame of the protein-coding region of the polynucleotide and preferably encode a polypeptide having no change, only a minor reduction, or an increase in NDR1 biological activity.

Amino-acid substitutions are preferably substitutions of single amino-acid residues. Insertions are preferably of about 1 to 10 contiguous nucleotides and deletions are preferably of about 1 to 30 contiguous nucleotides. Insertions and deletions are preferably insertions or deletions from an end of the protein-coding or noncoding sequence and are preferably made in adjacent base pairs. Substitutions, deletions, insertions or any combination thereof can be combined to arrive at a final construct.

Preferably, variant polynucleotides according to the present invention are "silent" or "conservative" variants. "Silent" variants are variants of a native NDR1 sequence or a homolog thereof in which there has been a substitution of one or more base pairs but no change in the amino-acid sequence of the polypeptide encoded by the polynucleotide. "Conservative" variants are variants of the native NDR1 polynucleotide or an allele or homolog thereof in which at least one codon in the protein-coding region of the polynucleotide has been changed, resulting in a conservative change in one or more amino-acid residues of the polypeptide encoded by the polynucleotide, i.e., an amino acid substitution. A number of conservative amino acid substitutions are listed below. In addition, one or more codons encoding cysteine residues can be substituted for, resulting in a loss of a cysteine residue and affecting disulfide linkages in the NDR1 polypeptide.

TABLE 1

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function are made by selecting substitutions that are less conservative than those listed above, e.g., causing changes in: (a) the structure of the polypeptide backbone in the area of the substitution; (b) the charge or hydrophobicity of the polypeptide at the target site; or (c) the bulk of an amino acid side chain. Substitutions generally expected to produce the greatest changes in protein properties are those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Polypeptides

"NDR1 Polypeptide". The term "NDR1 polypeptide" (or protein) refers to a polypeptide encoded by an NDR1 polynucleotide, including alleles, homologs, and variants of a native NDR1 polynucleotide. An NDR1 polypeptide can be produced by the expression of a recombinant NDR1 polynucleotide or can be chemically synthesized. Techniques for chemical synthesis of polypeptides are described, for example, in Merrifield, J. Amer. Chem. Soc. 85:2149–2156, 1963.

Polypeptide Sequence Homology. Ordinarily, NDR1 polypeptides encompassed by the present invention have at least about 70% amino acid similarity to a native NDR1 polypeptide, preferably at least about 80%, more preferably at least about 90%, and most preferably at least about 95% similarity. Such homology is considered to be "substantial homology," although more important than shared amino-acid sequence homology can be the common possession of characteristic structural features (including, for example, transmembrane domains, etc.) and the retention of biological activity that is characteristic of NDR1.

Polypeptide homology is typically analyzed using sequence analysis software such as the Sequence Analysis Software Package of the Genetics Computer Group, University of Wisconsin Biotechnology Center, Madison, Wis.). Polypeptide sequence analysis software matches homologous sequences using measures of homology assigned to various substitutions, deletions, substitutions, and other modifications.

"Isolated," "Purified," "Homogeneous" Polypeptides. A polypeptide is "isolated" if it has been separated from the cellular components (nucleic acids, lipids, carbohydrates, and other polypeptides) that naturally accompany it. Such a polypeptide can also be referred to as "pure" or "homogeneous" or "substantially" pure or homogeneous. Thus, a polypeptide that is chemically synthesized or recombinant (i.e., the product of the expression of a recombinant polynucleotide, even if expressed in a homologous cell type) is considered to be isolated. A monomeric polypeptide is isolated when at least 60% by weight of a sample is composed of the polypeptide, preferably 90% or more, more preferably 95% or more, and most preferably more than 99%. Protein purity or homogeneity is indicated, for example, by polyacrylamide gel electrophoresis of a protein sample, followed by visualization of a single polypeptide band upon staining the polyacrylamide gel; high pressure liquid chromatography; or other conventional methods.

Protein Purification. The polypeptides of the present invention can be purified by any of the means known in the art. Various methods of protein purification are described, e.g., in *Guide to Protein Purification*, ed. Deutscher, *Meth. Enzymol.* 185, Academic Press, San Diego, 1990; and Scopes, *Protein Purification: Principles and Practice*, Springer Verlag, N.Y., 1982.

Variant and Modified Forms of NDR1 Polypeptides. Encompassed by the NDR1 polypeptides of the present invention are variant polypeptides in which there have been substitutions, deletions, insertions or other modifications of a native NDR1 polypeptide. The variants substantially retain structural characteristics and biological activities of a corresponding native NDR1 polypeptide and are preferably silent or conservative substitutions of one or a small number of contiguous amino acid residues.

A native NDR1 polypeptide sequence can be modified by conventional methods, e.g., by acetylation, carboxylation, phosphorylation, glycosylation, ubiquitination, and labeling, whether accomplished by in vivo or in vitro enzymatic treatment of an NDR1 polypeptide or by the synthesis of an NDR1 polypeptide using modified amino acids.

Labeling. There are a variety of conventional methods and reagents for labeling polypeptides and fragments thereof. Typical labels include radioactive isotopes, ligands or ligand receptors, fluorophores, chemiluminescent agents, and enzymes. Methods for labeling and guidance in the choice of labels appropriate for various purposes are discussed, e.g., in Sambrook et al., 1989 and Ausubel et al., 1992.

Polypeptide Fragments. The present invention also encompasses fragments of an NDR1 polypeptide that lacks at least one residue of a native full-length NDR1 polypeptide. Preferably, such a fragment retains NDR1 activity, e.g., the ability to confer resistance to a plant pathogen when expressed as a transgene in a plant or possession of a characteristic functional domain, or an immunological determinant characteristic of a native NDR1 polypeptide. Immunologically active fragments typically have a minimum size of 7 to 17 or more amino acids. Preferably, NDR1 fragments are at least 10 amino acids in length, more preferably at least 20 amino acids, and most preferably, at least 30 amino acids.

Fusion Polypeptides. The present invention also provides fusion polypeptides including, for example, heterologous fusion polypeptides in which an NDR1 polypeptide sequence is joined to a fusion partner. Such fusion polypeptides can exhibit biological properties (such as substrate or ligand binding, enzymatic activity, antigenic determinants, etc.) derived from each of the fused sequences. Any conventional fusion partner can be used, including, for example, β-glucuronidase, β-galactosidase, etc. Fusion polypeptides are preferably made by the expression of recombinant nucleic acids produced by standard techniques.

Polypeptide Sequence Determination. The sequence of a polypeptide of the present invention can be determined by any of the various methods known in the art.

Polypeptide Coupling to a Solid Phase Support. The polypeptides of the present invention can be free in solution or coupled to a solid-phase support, e.g., nitrocellulose, nylon, column packing materials (e.g., Sepharose beads), magnetic beads, or glass wool, by conventional methods.

Antibodies

The present invention also encompasses polyclonal and/or monoclonal antibodies capable of specifically binding to an NDR1 polypeptide and/or fragments thereof. Such antibodies are raised against an NDR1 polypeptide or fragment thereof and are capable of distinguishing an NDR1 polypeptide from other polypeptides, i.e., they are NDR1-specific.

For the preparation and use of antibodies according to the present invention, including various immunoassay techniques and applications, see, e.g., Goding, *Monoclonal Antibodies: Principles and Practice*, 2d ed, Academic Press, New York, 1986; and Harlow and Lane, *Antibodies: A Laboratory Manual*, Cold Spring Harbor Laboratory, Cold Spring Harbor, N.Y., 1988. NDR1-specific antibodies are useful, for example in: purifying an NDR1 polypeptide from a biological sample, such as a host cell expressing a recombinant NDR1 polypeptide; in cloning an NDR1 allele or homolog from an expression library; as antibody probes for protein blots and immunoassays; etc.

NDR1 polypeptides and antibodies can be labeled by any of a variety of conventional methods. Suitable labels include, but are not limited to, radionuclides, enzymes, substrates, cofactors, inhibitors, fluorescent agents, chemiluminescent agents, magnetic particles, etc.

Obtaining Alleles and Homologs of NDR1

Based upon the availability of the NDR1 nucleotide sequence disclosed herein, alleles and homologs of the disclosed NDR1 sequence can be obtained by conventional methods, e.g., by screening a cDNA or genomic library with a probe that specifically hybridizes to a native NDR1 polynucleotide under at least moderately stringent conditions, by PCR or another amplification method using a primer or primers that specifically hybridize to a native NDR1 polynucleotide under at least moderately stringent conditions, or by identification of NDR1 alleles or homologs in an expression library using NDR1-specific antibodies.

Probes and primers based on the NDR1 sequence disclosed herein can also be used to obtain other plant disease resistance genes having substantial similarity to NDR1 by conventional methods.

Identifying Proteins that Interact with NDR1

NDR1 represents a strong candidate for a conserved signal transduction element required for avirulence gene-specific disease resistance. NDR1 interacts with numerous gene products involved in recognition and resistance to plant pathogens. The availability of the cloned NDR1 gene makes it possible to identify and clone genes encoding polypeptides that interact with NDR1 in the plant cell, including previously undiscovered plant disease resistance genes.

One method of identifying genes encoding polypeptides that interact with NDR1 is by means of the yeast two hybrid method, which has enjoyed broad application because of its relative ease for gene identification from DNA fusion libraries (Fields and Song, *Nature* 340:245–246, 1989; Chien et al., *Proc. Natl. Acad. Sci. (USA)* 88:9578–9582, 1991; Dalton and Treisman, *Cell* 72:223–232, 1993; Durfee et al., *Genes and Development* 7:555–569, 1993). The two hybrid system is based on targeting and identifying a protein-protein interaction through the use of a reporter system. For example, such a reporter system may employ the yeast Gal4 DNA-binding domain or the *E. coli* lexa DNA-binding domain and couple this region to a transcriptional activator such as Gal4 or VP16 that drives expression of a reporter molecule such as β-galactosidase or HIS3.

Plant Transformation and Regeneration

Nucleic-acid constructs that include an NDR1 polynucleotide are useful for producing pathogen-resistant plants, for example.

NDR1 polynucleotides can be expressed in plants or plant cells under the control of a suitable operably linked promoter, e.g., a promoter that is capable of expression in a cell of a particular plant. Any well-known method can be employed for plant cell transformation, culture, and regeneration in the practice of the present invention with regard to a particular plant species. Conventional methods for introduction of foreign DNA into plant cells include, but are not limited to: (1) Agrobacterium-mediated transformation (Lichtenstein and Fuller In: *Genetic Engineering*, Vol 6, Rigby, ed., London, Academic Press, 1987; and Lichtenstein and Draper, in: *DNA Cloning*, Vol II, Glover, ed., Oxford, IRl Press, 1985); (2) particle delivery (see, e.g., Gordon-Kamm et al., *Plant Cell* 2:603, 1990; or BioRad Technical Bulletin 1687); (3) microinjection (see, e.g., Green et al., *Plant Tissue and Cell Culture*, Academic Press, New York, 1987); (4) polyethylene glycol (PEG) procedures (see, e.g., Draper et al., *Plant Cell Physiol*. 23:451, 1982); Zhang and Wu, *Theor. Appl. Genet*. 76:835, 1988); (5) liposome-mediated DNA uptake (see, e.g., Freeman et al., *Plant Cell Physiol*. 25:1353, 1984); (6) electroporation (see, e.g., Fromm et al., *Nature* 319:791, 1986); and (7) vortexing methods (see, e.g., Kindle, Proc. *Natl. Acad. Sci. USA* 87:1228, 1990).

The term "plant" encompasses any higher plant and progeny thereof, including monocots (e.g., lily, corn, rice, wheat, barley, etc.), dicots (e.g., tomato, potato, soybean, cotton, tobacco, etc.), and includes parts of plants, including reproductive units of a plant (e.g., seeds, fruit, flowers, etc.)

A "reproductive unit" of a plant is any totipotent part or tissue of the plant from which one can obtain a progeny of the plant, including, for example, seeds, cuttings, tubers, buds, bulbs, somatic embryos, cultured cells (e.g., callus or suspension cultures), etc.

An NDR1 transgene is useful for conferring resistance to a plant pathogen on plants that would otherwise be susceptible to the pathogen. Several cloned plant host resistance genes confer disease resistance to transgenic plants. For example, the N gene of tobacco confers resistance to the viral pathogen TMV (Whitham et al., *Cell* 78:1101–1115, 1994); the RPM1 gene of Arabidopsis confers resistance to *Pseudomonas syringae* strains carrying the avrRpm1 avirulence gene (Grant et al., *Science* 269:843–846, 1995; and the L6 gene of flax confers resistance to flax rust, a fungal pathogen (Lawrence et al., *Plant Cell* 7:1195–1206, 1995).

Expression of NDR1 in transgenic plants confers resistance to the bacterial pathogens *Pseudomonas syringae* pv. *tomato* and *P. syringae* pv. *maculicola*, the fungal pathogen *Peronospora parasitica*, and, in addition to a wide variety of other phytopathogens, including, but not limited to, bacteria, viruses (e.g., tobacco mosaic virus, potato virus X, etc.), fungi (e.g., *Phytophthora infestans*, Fusarium spp., etc.), and nematodes (e.g., root knot nematode, etc.). To confer such broad-spectrum pathogen resistance, it is preferable to express an NDR1 transgene at high levels, e.g., through expression of multiple copies of the NDR1 transgene and/or the use of strong promoters to drive expression. Alternatively, a mutation in NDR1 that causes constitutive expression may be used to provide broad-spectrum pathogen resistance. Expression of an NDR1 transgene in plant cells at a sufficiently high level may initiate the plant defense response constitutively in the absence of signals from the pathogen. The level of mRNA and polypeptide expression can be determined by conventional methods. NDR1 transgene expression can be driven by its own promoter or by a heterologous promoter. Constitutive expression is preferred, although inducible or tissue-specific promoters, for example, can be used to limit the temporal and tissue expression of a defense response.

An NDR1 polynucleotide can be co-expressed in a plant cell together with one or more cloned specific resistance genes and/or avirulence genes.

The invention will be better understood by reference to the following Example, which are intended to merely illustrate the best mode now known for practicing the invention. The scope of the invention is not to be considered limited thereto.

EXAMPLE

The Arabidopsis NDR1 locus is required for resistance to both the bacterial pathogen *Pseudomonas syringae* pv. *tomato* and the fungal pathogen *Peronospora parasitica* (Century et al., *Proc. Natl. Acad. Sci. USA*, 92:6597–6601, 1995, incorporated herein by reference). Mutation of the NDR1 locus causes broad spectrum susceptibility to these pathogens, regardless of race or strain. Thus, NDR1 represents a strong candidate for a conserved signal transduction element required for avirulence (avr) gene-specific disease resistance.

Figure 1:
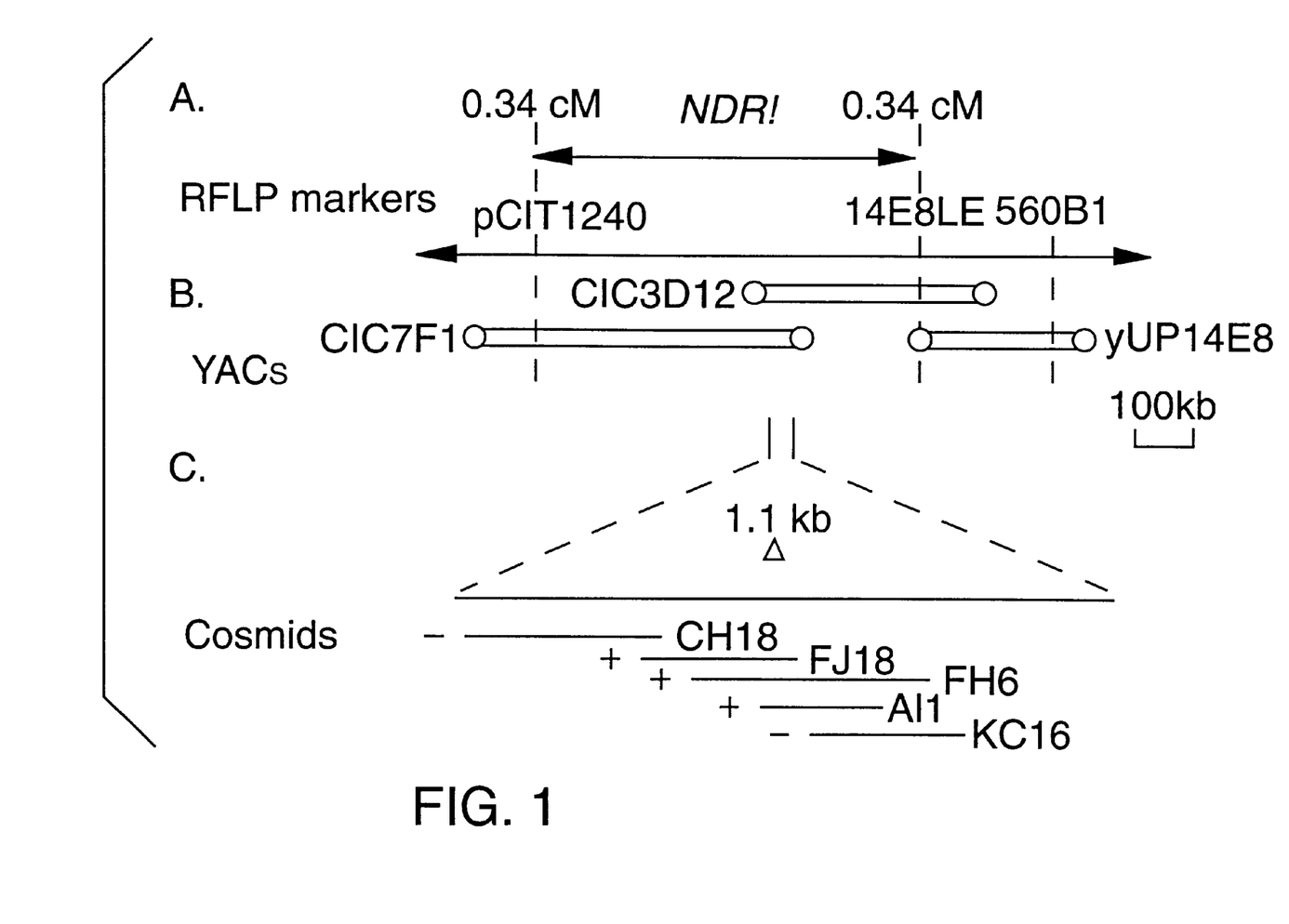
FIG. 1A shows a fine structure RFLP map with restriction fragment length polymorphism (RFLP) markers tightly linked to NDR1.
FIG. 1B shows yeast artificial chromosomes (YACs) from which a YAC contig spanning the region containing the NDR1 gene was constructed.
FIG. 1C shows a cosmid contig with cosmids derived from CIC3D12 organized into an overlapping set that spanned NDR1. The approximately 1 kb deletion in *A. thaliana* mutant nrd1-1 is indicated. Cosmids that complemented (+, HR restored) or did not complement (−, no HR) the nrd1-1 mutation are indicated.

NDR1 is located on Arabidopsis chromosome three, in an interval of approximately 8.5 cM between restriction fragment length polymorphism (RFLP) markers g6220 and g4711 (Century et al., *Proc. Natl. Acad. Sci. USA*, 92:6597–6601, 1995). Fine-structure mapping with RFLP and polymerase chain reaction (PCR) based markers further delimited the genomic region carrying NDR1 (FIG. 1A). A segregating population from a cross between Col-0 ndr1-1/ndr1-1 and La-er NDR1/NDR1 plants was used for genetic mapping. Molecular markers were obtained from the Arabidopsis Biological Resource Center (Ohio State University) and mapped relative to NDR1. Flanking PCR markers nga162 (Konieczny and Ausubel, *Plant J.* 4:403, 1993) and gl1 (Whalen et al., *Plant Cell* 3:49, 1991) (22 cM apart) were used to rapidly prescreen large numbers of susceptible F2 plants for recombinants. F3 families from recombinant plants were then used to identify recombination events between RFLP markers tightly linked to NDR1 and verify the genotype of the recombinants by disease assays (Ecker, *Methods: A Companion to Methods in Enzymology* 1:186, 1990; Ward and Jen, *Plant Mol. Biol.* 14:561, 1990; Grill and Somerville, *Mol. Gen. Genet.* 226:484, 1991; Creusot et al., *Plant J.* 8:763, 1995).

Two tightly linked, flanking markers, RFLP marker pCIT1240 and ARMS marker 560B1, were identified and used as hybridization probes against four yeast artificial chromosome (YAC) libraries (Schmidt et al., *Aus. T. Plant Phys.* 19:341, 1992) of Arabidopsis accession Col-0 genomic DNA to isolate YAC clones in the region surrounding NDR1. Ends of the insert DNA from the YAC clones were isolated from the YAC clones by inverse PCR and plasmid rescue as described (Bent et al., *Science* 265:1856, 1994) and were converted to RFLP markers for genetic mapping. The contig was extended until an overlapping set of YAC clones was constructed that linked the clones identified with 560B1 to those that hybridized with pCIT1240 (FIG. 1B). An RFLP marker (14E8LE) derived from one end of yUP14E8 narrowed the physical genomic region containing NDR1 to a 0.68 cM interval.

Recombinant breakpoint analysis determined that NDR1 was contained within the contig. However, due to the low frequency of recombination (~1 cM/1050 kb) in this region of the genome, at least one end of each YAC clone cosegregated with NDR1 in the mapping population. It was therefore impossible to identify a single YAC clone that spanned the locus.

Two YAC clones, CIC3D12 and CIC7E1, together spanned NDR1, as determined by recombination analysis. A plant-transformation competent cosmid library from each of these two YAC clones was generated (FIG. 1C). For construction of cosmid libraries, yeast DNA from CIC3D12 and CIC7E1 was partially digested with Sau3A, size fractionated (to 15 to 20 kb), and cloned into the BamHI site of the binary vector pCLD04541 (Bechtold et al., *R. Acad. Sci. Paris Life Sci.* 316:1194, 1993). Clones carrying Arabidopsis DNA were isolated by hybridization with RFLP markers that cosegregated with NDR1. Cosmids were organized into overlapping contig islands by restriction analysis and hybridization patterns.

A DNA gel blot demonstrated a deletion of approximately 1 kb in the mutant ndr-1. A 14 kb EcoRI Arabidopsis DNA fragment from cosmid FH6 was radiolabeled and used as a hybridization probe against HindIII digested Col-0, La-er, or ndr1-1 genomic DNA. The ndr1-1 lane showed a deletion of approximately 1 kb containing a HindIII site resulting in a larger 1.9 kb single fragment.

The discovery of the deletion in the area spanned by cosmid FH6 focused our efforts on cosmids in that region. One cosmid from the CIC3D12 library, FH6, uncovered a genetic alteration in the ndr1-1 mutant plant (Century et al., *Proc. Natl. Acad. Sci. USA*, 92:6597–6601, 1995). Further DNA blot analysis proved that a 1.1-kb fragment on the FH6 cosmid clone was deleted in the fast-neutron-generated ndr1-1 mutant. To determine if the 1.1-kb deletion was responsible for the susceptible phenotype, ndr1-1 plants were transformed with the cosmids in the contig surrounding the deletion (FIG. 1C). Agrobacterium-mediated transformation of ndr1-1 plants was performed using the vacuum infiltration procedure of Bechtold et al. (ibid.), with modifications as described by Bent et al. (*Science* 265:1856, 1994). T1 seeds were surface-sterilized and transformants were selected on agar-solidified MS medium containing kanamycin (40 mg/ml). After one week, green plants were transferred to potting mix and inoculated after three to five weeks growth. The hypersensitive response (HR) assay used to test for complementation is described by Kunkel et al. (*Plant Cell* 5:865, 1993). Restoration of NDR1 activity was determined by inoculating transformants with high concentrations of *P. syringae* pv. *maculicola* (*Psm*) expressing the avirulence gene avrRpt2. Wild-type Col-0 plants react with a HR to *Psm*, while ndr1-1 mutant plants do not. The *Psm* strain lacking an avirulence gene recognized by Arabidopsis plants causes a null response in the HR assay and was used as a control inoculation. ndr1-1 plants transformed with FH6, as well as several other cosmids spanning the deletion, restored the wild-type HR to *Psm*(avrRpt2) in ndr1-1 plants, but did not restore a wild-type HR to *Psm* lacking an avirulence gene (FIG. 1C). Linked cosmids that lacked the region encompassed by the deletion did not restore the HR resistance response in ndr1-1 plants. Thus, the region encoding NDR1 was delimited to a 3.5 kb section. These results indicated that NDR1 was encoded in a region carried by all of the complementing cosmids.

Figure 2:
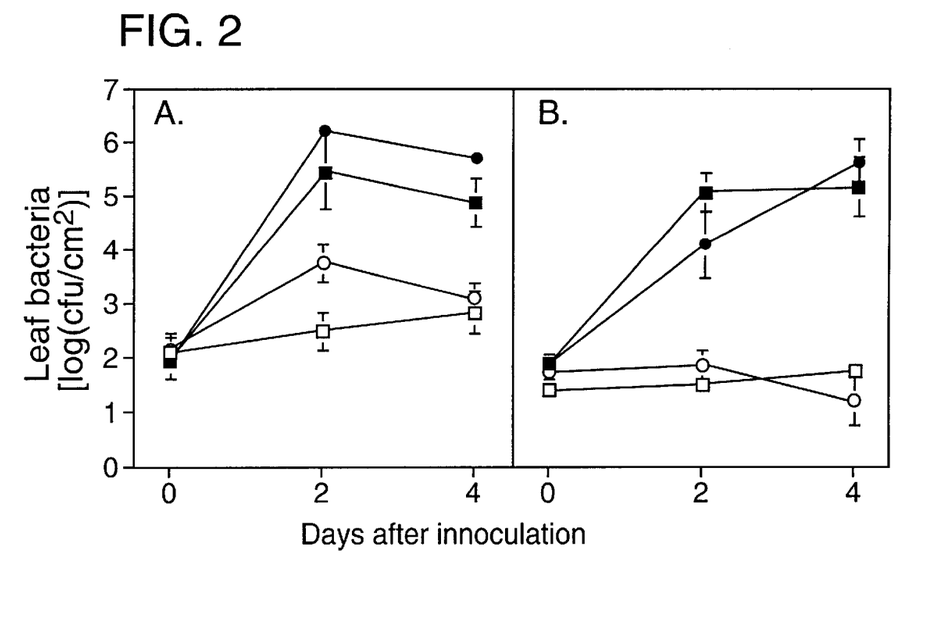

In planta bacterial growth analyses were performed (FIG. 2). T3 homozygous plant lines (ndr1-1 Arabidopsis transformed with the non-complementing CB17 cosmid (which does not contain the NDR1 ORF) or with the complementing FH6 cosmid were derived from selfing progeny of a single Col-0 ndr1-1/ndr1-1 transformant heterozygous for kanamycin resistance. These plant lines, as well as the ndr1-1 mutant and wild-type Col-0 were inoculated by vacuum infiltration with *Pst* DC3000 (avrRpt2) or *Pst* DC3000 (avrRpm1), and bacterial growth in leaves was monitored as described (Whalen et al., *Proc. Natl. Acad. Sci. USA* 85:6743, 1988). Also, cotyledon sporulation assays with *Peronospora parasitica* (Holub et al., *Mol. Plant-Microbe Interact.* 7:223, 1994) (Table 1) were performed. Both the in planta bacterial growth analyses and cotyledon sporulation assays demonstrated restored, heritable resistance in the complemented transformed plants.

To sequence genomic DNA spanning the deletion in the ndr1-1 mutant, cosmid FH6 DNA was sonicated and fragments of approximately 1 kb were size selected on agarose gels, purified using GeneClean (Bio 101), and subcloned into the EcoRV site of pBluescript (Stratagene). Two HindIII fragments that spanned the deletion were isolated from FH6, radiolabeled, and used as probes against the subclones. DNA sequences from these subclones were obtained by the cyclic reaction termination method using fluorescently labeled dideoxyribonucleotide triphosphates and following the instructions provided with the PRISM Ready Reaction DyeDeoxy Terminator Cycle Sequencing Kit (Perkin Elmer Corporation). DNA Sequencing Analysis (version 2.01) and SeqEd (version 1.03) were used to process raw sequence data. Sequences were aligned and analyzed using Sequencher 3.0 for the Macintosh.

Figure 4:
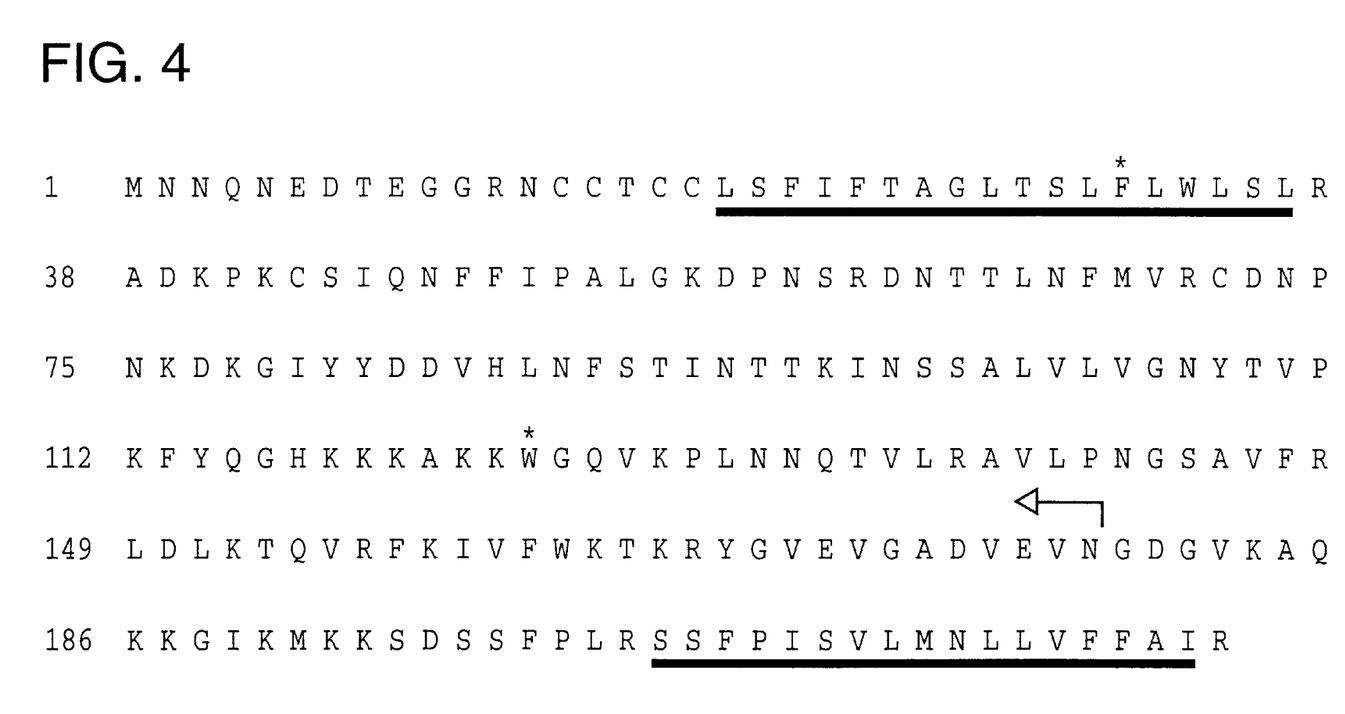

Sequencing of wild-type Col-0 genomic DNA revealed a single 660-bp open reading frame (ORF) in the region corresponding to the 1.1-kb deletion in the ndr1-1 mutant. Sequencing of the additional mutant alleles ndr1-2 and ndr1-3 also revealed alterations in this 660 bp ORF (FIG. 4). The nucleotide sequence of the 660-bp ORF, including 162 bp of the 5'-flanking sequence and 140 bp of 3'-flanking sequence, and the deduced amino-acid sequence of NDR1 (in standard one-letter code) are shown in FIG. 3 (and in standard three-letter code in SEQ ID NO:1 and SEQ ID NO:2). The 660-bp ORF predicts a 219 amino acid gene product (FIG. 3; SEQ ID NO:1 and SEQ ID NO:2) that shows identity to one Arabidopsis expressed sequence tag (EST) (accession number T21313).

Figure 5:
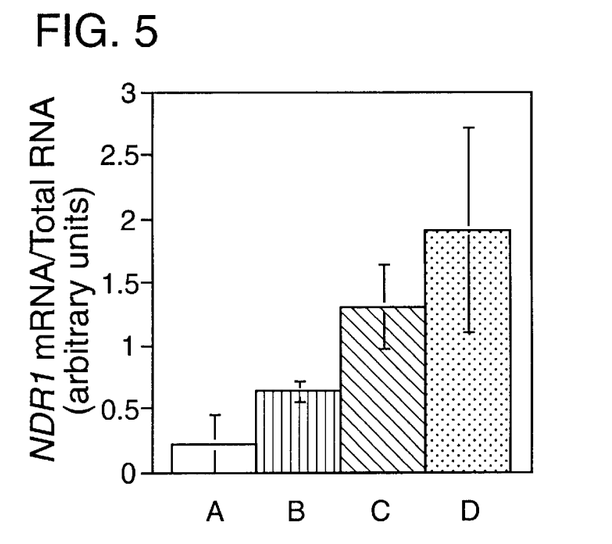
FIG. 5 is a graph of RNA gel blot analyses showing NDR1 mRNA accumulation after 8 hours in uninoculated tissue (A), leaves infiltrated with $MgCl_2$ blank (B), virulent DC3000 (C) or avirulent DC3000 avrRpt2 (D). Data from three independent RNA gel blots were combined and standardized for loading by comparing with control probes for total RNA.

The cDNA clone T21313 corresponding to the EST was obtained from the Arabidopsis Biological Resource Center and was used to probe RNA gel blots. Five week old plants grown under short day conditions in a growth chamber were vacuum infiltrated with a 10 nM $MgCl_2$ blank, $1 \times 10^7$ cfu/ml virulent Pst DC3000, or $1 \times 10^7$ cfu/ml avirulent Pst DC3000avrRpt2. Plants were frozen in liquid nitrogen after an 8 hour induction period and total RNA was extracted (Tri-Reagent, Sigma). Gel blot analysis was performed according to a standard protocol (Ausubel et al., *Current Protocols in Molecular Biology*, Wiley-Interscience, New York, 1992) using a Hybond-NX transfer membrane (Amersham) according to manufacturer's directions. The blot was stripped and re-probed with pea 18S ribosomal DNA (Jorgensen et al., *Plant Mol. Biol.* 8:3, 1987) as a control for loading. Data was generated by combining the results from three separate RNA gel blots and standardized for loading by comparison with control probes for total RNA (FIG. 5). A similar trend of RNA accumulation was seen in plants inoculated with DC3000 avrB in two separate experiments.

The size of the hybridizing RNA from wild-type Col-0 plants is in agreement with the size of the ORF, indicating that the full-length gene is contained in the single ORF without introns. The message is absent in ndr1-1 mutant plants. Accumulation of NDR1 mRNA is upregulated in wild-type Col-0 plants by both avirulent and virulent bacteria relative to the $MgCl_2$ blank treatment and in ndr1-2 and ndr1-3. The sequences of these ndr1 alleles both contain alterations in the putative ORF. Upregulation of NDR1 is seen as early as four hours after inoculation, with maximal expression at 8 hours. NDR1 is therefore a classically induced defense response gene that is genetically required for resistance.

Analysis of the predicted amino-acid sequence of NDR1 using the SBASE library (Pongor et al., *Nucleic Acids Res.* 22:3610, 1994) identified two putative transmembrane domains that are similar (up to 85%) to known membrane-spanning domains in proteins such as the 6K protein of Ockelbo virus (a Sindbis virus) and the inositol 1,4,5-triphosphate receptor (IP3R) protein from various species. In NDR1, the putative transmembrane domains span amino acids 19 to 36 and 202 to 218 (FIG. 4). These homologies suggest that NDR1 is a membrane-associated protein. In ndr1-1 the entire amino-terminal portion of the protein through N-179 (indicated by the arrow in FIG. 4) is deleted, as well as a portion of the upstream DNA (see GenBank accession #AF021346, incorporated herein by reference).

BLAST searches (Altschul et al., *J. Mol. Biol.* 215:403, 1990) revealed limited similarity with two tobacco genes, hin1 (Gopalan et al., *Plant J.* 10:591–600, 1996) and clone NG2 (Karrer et al., *Plant Mol. Biol.* in press, 1997), which are correlated with the resistance response. With hin1, there are three regions of similarity to NDR1: amino acids 20–42, which contain the first putative transmembrane domain, display 60% similarity, including conservative substitutions; amino acids 73–85, which display 69% similarity; and amino acids 113–118, which display 100% identity. When compared with clone NG2, from amino acids 146–167 there is 86% similarity to NDR1. Both hin1 (Gopalan et al., *Plant J.* 10:591–600, 1996) and NDR1 are induced by avirulent pathogens.

In subsequent experiments a constitutive plant promoter was fused to the NDR1 cDNA and this construct was transformed into wild-type Col-0 and ndr1-1 mutant plants. Transformants were carried to homozygosity and analyzed by hand inoculation assays and growth curves (where levels of bacterial growth in the plant was directly measured). In hand inoculation assays, ndr1-1 plants that overexpressed the NDR1 gene (as shown by RNA gel blot analyses) exhibited an enhanced disease resistance response. Whereas wild-type and ndr1-1 plants inoculated with *Pseudomonas syringae* pv. maculicola show disease symptoms (water soaked lesions and chlorosis) after approximately 5 days, ndr1-1 mutant plants that overexpressed the wild-type NDR1 gene displayed a HR. This response was manifested by a HR-like phenotype (Delaney, *Plant Physiol.* 113:5–12, 1997), in which small necrotic lesions form spontaneously on the leaves, which is an indicator that the plants are resistant to a variety of bacterial pathogens that would normally be virulent. In growth curves, an ndr1-1 plant line that overexpresses the NDR1 gene showed very significant reductions in growth of Pst DC3000 (three orders of magnitude lower) compared with wild-type plants.

NDR1 is required for resistance to the bacterial pathogen Pst expressing avrB, avrRpm1, or avrPph3, as well as resistance to numerous isolates of the fungal pathogen *Peronospora parasitica* (Century et al., *Proc. Natl. Acad. Sci. USA*, 92:6597–6601, 1995), but not for expression of the resistance gene RPS2. NDR1 may encode a component in the signal transduction pathway downstream of initial recognition of an avirulent pathogen. Mutation of NDR1 results in loss of resistance governed by several resistance genes. Because of their specificity, resistance gene products may act as receptors for avirulence signals. NDR1 may interact directly with specific receptors to transduce the elicitor signal, or it may serve as a transporter or receptor for an elicitor signal or secondary messenger.

Several genes are required for the activity of individual resistance genes in tomato and barley (Hammond-Kosack et al., *Plant Cell* 6:361, 1994; Salmeron et al., *Cell* 86:123, 1996; Freialdenhoven et al., *Plant Cell* 8:5, 1996). However, NDR1 and another Arabidopsis gene, EDS1 (Parker et al., *Plant Cell* 8:2033, 1996), are necessary for plant defense mediated by numerous resistance genes. The fact that mutation of NDR1 results in susceptibility to both bacterial and fungal pathogens strongly supports a central role for NDR1 in disease resistance.

What is claimed is:

1. An isolated polypeptide comprising an amino acid sequence having at least 70% sequence identity to the sequence as set forth as SEQ ID NO: 2, wherein the polypeptide increases resistance to a bacterial or fungal pathogen when expressed in a plant, and wherein the amino acid sequence of the polypeptide comprises amino acids 1–179 of SEQ ID NO: 2.

2. The isolated polypeptide of claim 1 comprising an amino acid sequence having at least 80% sequence identity to the sequence as set forth as SEQ ID NO: 2.

3. The isolated polypeptide of claim 1 comprising an amino acid sequence having at least 90% sequence identity to the sequence as set forth as SEQ ID NO: 2.

4. The isolated polypeptide of claim 1 comprising an amino acid sequence having at least 95% sequence identity to the sequence as set forth as SEQ ID NO: 2.

5. The isolated polypeptide of claim 1 comprising the amino acid sequence as set forth in SEQ ID NO: 2 or a conservative amino acid substitution thereof.

6. The isolated polypeptide of claim 1 comprising the amino acid sequence as set forth in SEQ ID NO: 2 or a single conservative amino acid substitution thereof.

7. The isolated polypeptide of claim 1 comprising the amino acid sequence as set forth in SEQ ID NO: 2.

8. An isolated polypeptide comprising at least 10 contiguous amino acids of the sequence as set forth in SEQ ID NO: 2, wherein the polypeptide increases resistance to a bacterial or fungal pathogen when expressed in a plant.

9. The isolated polypeptide of claim 8 comprising at least 20 contiguous amino acids of the sequence as set forth as SEQ ID NO: 2.

10. The isolated polypeptide of claim 8 comprising at least 30 contiguous amino acids of the sequence as set forth as SEQ ID NO: 2.

11. An isolated polypeptide encoded by a nucleic acid molecule that hybridizes with a nucleic acid probe comprising the open reading frame of SEQ ID NO: 1, under wash conditions of 65° C., 0.5×SSC and 0.5% SDS for 1 hour, wherein the polypeptide increases resistance to a bacterial or fungal pathogen when expressed in a plant.

12. An isolated polypeptide encoded by a nucleic acid molecule that hybridizes with a nucleic acid probe comprising the open reading frame of SEQ ID NO: 1, under wash conditions of 60° C., 0.5×SSC and 0.5% SDS for 1 hour, wherein the polypeptide increases resistance to a bacterial or fungal pathogen when expressed in a plant.

13. An isolated polypeptide encoded by a nucleic acid molecule that hybridizes with a nucleic acid probe comprising the open reading frame of SEQ ID NO: 1, under wash conditions of 55° C., 0.5×SSC and 0.5% SDS for 1 hour, wherein the polypeptide increases resistance to a bacterial or fungal pathogen when expressed in a plant.

14. An isolated polypeptide encoded by a nucleic acid molecule that hybridizes with a nucleic acid probe comprising the open reading frame of SEQ ID NO: 1, under wash conditions of 50° C., 0.5×SSC and 0.5% SDS for 1 hour, wherein the polypeptide increases resistance to a bacterial or fungal pathogen when expressed in a plant.

15. An isolated polypeptide comprising amino acids 1–179 of SEQ ID NO: 2, wherein the polypeptide increases resistance to a bacterial or fugal pathogen when expressed in a plant.

* * * * *

UNITED STATES PATENT AND TRADEMARK OFFICE
CERTIFICATE OF CORRECTION

PATENT NO.    : 6,579,677 B1
DATED         : June 17, 2003
INVENTOR(S)   : Staskawicz et al.

It is certified that error appears in the above-identified patent and that said Letters Patent is hereby corrected as shown below:

Column 13,
Line 28, "DNA" should read -- cDNA --.
Line 36, "lexa" should read -- lexA --.

Column 24,
Line 9, "fugal" should read -- fungal --.

Signed and Sealed this

Twenty-first Day of October, 2003

JAMES E. ROGAN
*Director of the United States Patent and Trademark Office*